United States Patent [19]

Wolfe et al.

[11] Patent Number: 5,049,255

[45] Date of Patent: Sep. 17, 1991

[54] OXYGEN SENSING UNIT

[75] Inventors: Michael J. Wolfe, Villa Ridge; Robert F. Killion, Florissant, both of Mo.

[73] Assignee: Tomco, Incorporated, St. Louis, Mo.

[21] Appl. No.: 487,159

[22] Filed: Mar. 1, 1990

[51] Int. Cl.⁵ .................................... G01N 27/409
[52] U.S. Cl. .................................... 204/428; 204/424
[58] Field of Search ............ 204/427, 428, 429, 153.18

[56] References Cited

U.S. PATENT DOCUMENTS

| | | | |
|---|---|---|---|
| 4,121,989 | 10/1978 | Shum et al. | 204/428 |
| 4,127,464 | 11/1978 | Ichikawa et al. | 204/428 X |
| 4,141,813 | 2/1979 | Kita et al. | 204/428 |
| 4,152,232 | 5/1979 | Otsuka et al. | 204/428 X |
| 4,184,934 | 1/1980 | Bode et al. | 204/428 |
| 4,756,885 | 7/1988 | Raff et al. | 204/428 X |
| 4,824,550 | 4/1989 | Ker et al. | 204/427 |
| 4,842,713 | 6/1989 | Stahl | 204/428 |
| 4,897,174 | 1/1990 | Wang et al. | 204/425 |

Primary Examiner—T. Tung
Attorney, Agent, or Firm—Polster, Polster and Lucchesi

[57] ABSTRACT

In an oxygen sensing unit, an oxygen sensing cell with a closed outer end is encircled by a side wall of a protective shell or shield, and recessed from an open mouth of the shell. The cell and shell are mounted in a plug made up of a closure cap with an externally threaded section and a plug body with an internally threaded section complementary to the externally threaded section of the closure cap, the two parts of the plug cooperating to hold and compress the shell and cell, mediately or immediately, and permit the removal and replacement of the cell.

11 Claims, 5 Drawing Sheets

OXYGEN SENSING UNIT

Background of the Invention

This invention has particular, but not exclusive application to automotive exhaust oxygen sensors. Such sensors are well known. Typically, they consist of a closed-end tube or cell of stabilized zironia ceramic, containing a rare earth oxide stabilizer. Both the inner surface of the sensor and its exposed outer surface are coated with porous catalytic electrodes, usually platinum. The inner electrode is situated so that a constant supply of air from the ambient atmosphere is maintained in contact with it. The air provides a constant oxygen partial pressure reference. The outer electrode is exposed to the exhaust stream the oxygen content of which is to be measured. The outside electrode is coated with a protective layer, and is electrically connected to a metal plug by means of an outer stripe of electrically conductive material. The inner electrode layer is connected by a lead wire to an electrical circuit bridging the two electrodes and by which the voltage between the two electrodes is determined and used to control the air-fuel ratio of the engine. The cell has been shielded from damage by a metal shell. However, it has been thought necessary to have openings, typically elongated axial slots, of substantial area, in the side walls of the metal shell to permit access of the exhaust gases to the outer surface of the cell for quick response. An example of such an arrangement is found in U.S. Pat. No. 4,155,827, which also gives a good discussion of such cells and their operation. The slots have exposed the cell to bombardment by carbon and other particles along its length, which leads to the deterioration of the cell.

It has been found that a shell can be provided in the form of a cylinder with no openings at all in its side wall or with a relatively small slot area extending radially from the cell and positioned in a special relationship to a portion of a body of a plug that may be an integral part of the shell. The closed end of the cell can be spaced inwardly from the outer end of the cylindrical shell, and still the cell can respond as quickly as it does in a shell with conventional axial slots in its side, but the cell is largely protected from carbon bombardment.

Upon failure of the cell, heretofore it has been considered necessary to replace the entire unit, cell, shell, plug and all, which has been expensive.

One of the objects of this invention is to provide an oxygen sensor in which the cell can be replaced easily and economically.

Another object is to provide such a unit which gives long life, and at least as great efficiency as oxygen sensors known heretofore.

Other objects will be apparent to those skilled in the art in light of the following description and accompanying drawings.

SUMMARY OF THE INVENTION

In accordance with this invention, generally stated, in an oxygen sensing unit having an oxygen sensing hollow cell with a closed inner end, and a protective shell, the shell has a side wall that is either imperforate or has a radial slot positioned closely adjacent a chamfered edge of a body element of a plug, of which the shell may be an integral part, and an open inner end, the cell being surrounded by the side wall but spaced therefrom through a major portion of its length. The inner end of the cell terminates short of the open inner end of the shell. The plug has an externally threaded closure cap and an internally threaded body. The cell is removably and replaceably mounted in the plug with parts thereof compressed, mediately or immediately, between the cap and the body.

DESCRIPTION OF THE PREFERRED EMBODIMENTS

Referring now to the drawing, and particularly to FIGS. 1–8, for one illustrative embodiment of oxygen sensor unit of this invention, reference numeral 1 indicates a complete unit which, in this embodiment, is made up of a cell 2, a shell or shield 3, a plug 4 made up of a body 5 and closure cap 6, a ceramic sleeve 7, a clip-terminal 8, washers 11 and 13, and a lead wire 15.

Figure 1:
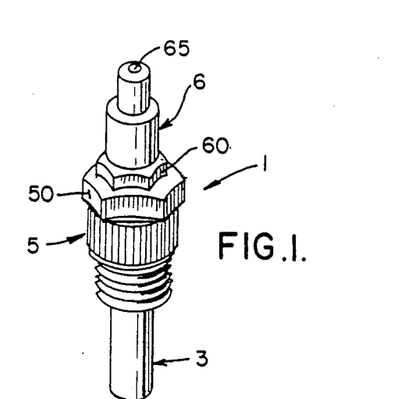
FIG. 1 is a view in perspective of one embodiment of oxygen sensor of this invention.
Figure 2:
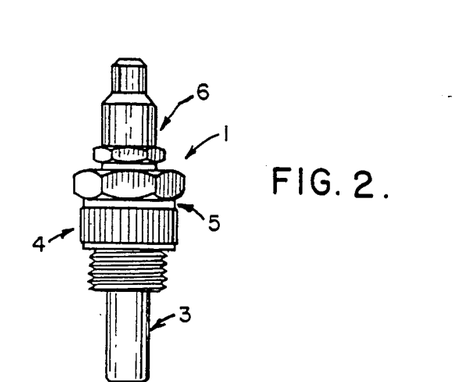
FIG. 2 is a view in side elevation.
Figure 3:
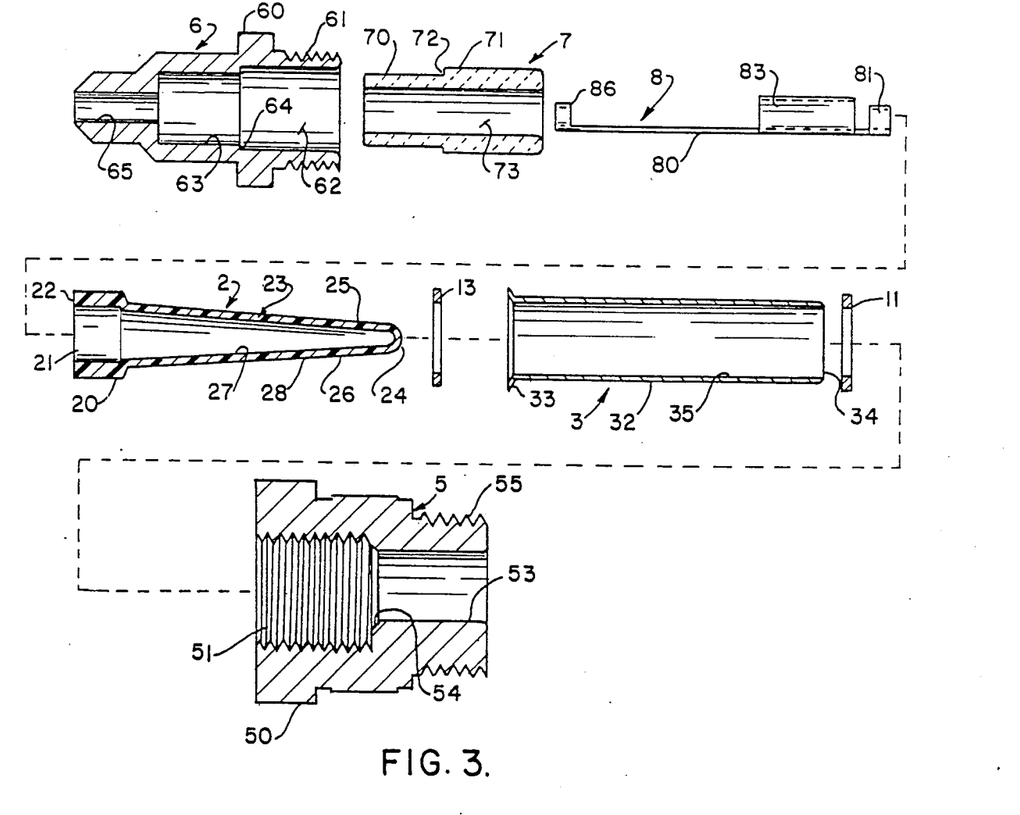
FIG. 3 is an exploded sectional view of the device shown in FIGS. 1 and 2.
Figure 4:
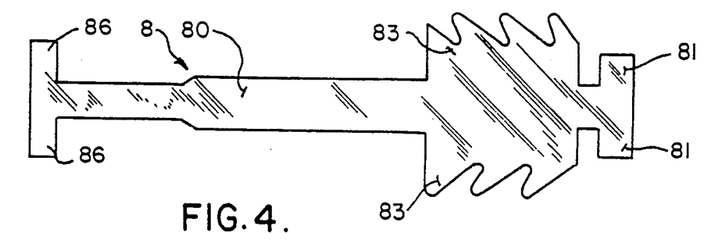
FIG. 4 is a top plan view of a terminal-connector as it is stamped from a sheet.
Figure 5:
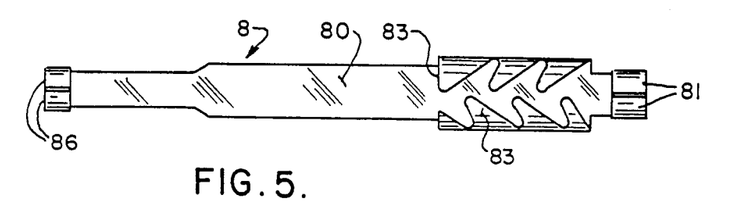
FIG. 5 is a top plan view of the connector of FIG. 4 in condition to be crimped to a terminal lead wire.
Figure 6:
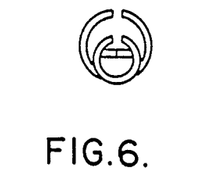
FIG. 6 is a view in end elevation looking from right to left in FIG. 5.
Figure 7:
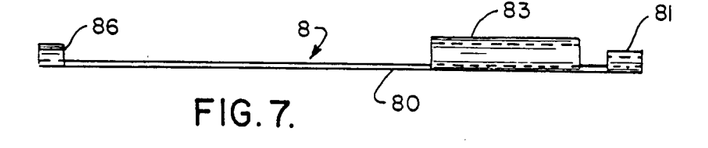
FIG. 7 is a view in side elevation of the device shown in FIG. 5.
Figure 8:
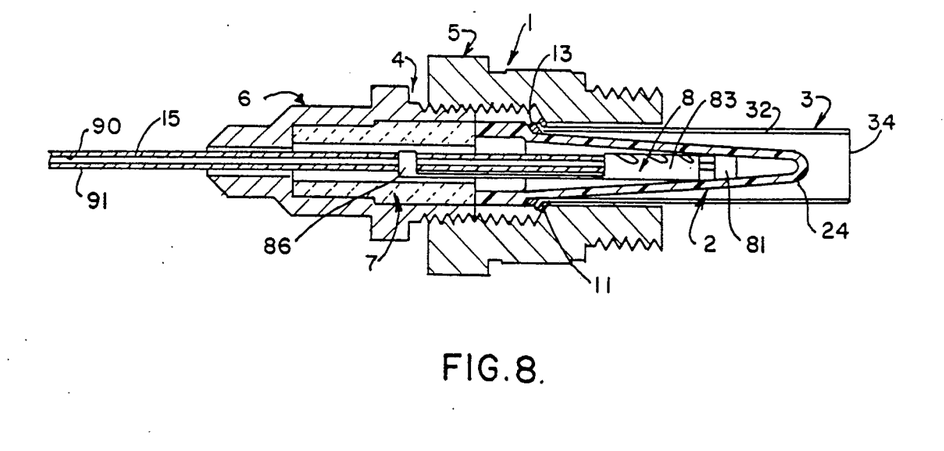
FIG. 8 is a longitudinal sectional view of an assembled oxygen sensor of this invention.

The cell 2 has a collar section 20 at an outer end, with an open mouth 21 defined by an edge of a flat surface 22, a tapered section 23, and a closed nose 24 at the inner end of the cell. The cell has an inner surface 25 and an outer surface 26, an inner electrode 27 and an outer electrode 28, and in these respects, the cell is conventional. The shell or shield 3 is a cylindrical tube of metal as, for example, stainless steel, with an imperforate side wall 32 flared at its outer end to form a lip 33, and slightly chamfered at its inner end where an inner surface 35 of the tube defines an open inner mouth 34.

The plug body 5 has hex flats 50 at its outer end, around an internally threaded passage section 51, concentric with and forming a continuous passage with an inner passage 53 which is of less diameter than the section 51, the walls defining the sections 51 and 53 defining between them a chamfered shoulder 54. The inner end of the body 5 has an externally threaded section by which it can be screwed into a standard tapped hole or fitting in the automobile exhaust system.

The closure-cap 6 also has hex flats 60, to take a wrench. The flats 60 are located intermediate the ends of the closure. Inboard of the flats, the closure has a cylindrical, externally threaded section 61, complementary to the internally threaded section 51 of the body 5. The closure has a passage extending entirely through it, in three stages. An innermost section 62 has the largest diameter; an intermediate section 63 has a smaller diameter than the innermost section 62, to define between them a shoulder 64, and a lead wire section 65 has the smallest diameter.

The ceramic sleeve 7 has a straight passage 73 through it. On its external surface, it has a neck 70, a body 71 of larger diameter, and between the neck and body, a shoulder 72.

The clip-terminal 8 has a connecting strap 80, outer, bare conductor engaging wings 86, wire gripping serrated wings 83, and inner wings 81.

The lead wire 15 has a central conductor 90 covered with insulation 91.

The assembly of the sensor unit is simple. The insulation 91 of the lead wire is stripped away at its inner end, and the lead wire is threaded through the passage 65 of the cap 6, and the passage 73 of the ceramic sleeve 7, and is crimped into the clip-terminal 8, with the wings 81 in tight mechanical and electrical contact with the exposed conductor 90. The insulation can be stripped back as far as the inner wings 86 if desired, because, as can be seen from FIG. 8, the lead wire is insulated from the plug 4 by the ceramic sleeve, beyond the outer wings 86. The clip terminal wings 81 and 83 are then forced into intimate mechanical and electrical contact with the inner electrode surface 27 of the cell 2. The washer 11 is slipped on to the shell 3 until it engages the inner surface of the lip 33. The washer 13 is mounted on the cell 2, against an external shoulder formed between the collar 20 and the tapered part 23, the shell or shield 3 is placed over the tapered portion 23 of the cell, the plug body 5 is placed over the shell and cell, with washer 11 seated on the shoulder 54, the closure cap 6, with the ceramic sleeve 7 seated in it as shown in FIG. 8 is then mounted in the body 5, again as illustrated in FIG. 8, and the assembly is complete.

In order to replace the cell, it is only necessary to unscrew the cap 6, to remove the cell from the shell 3 and from the end of the lead wire, replace the cell and remount it as has been indicated.

It can be seen that when the unit 1 is installed in an exhaust system in the conventional way, the shield 3 will extend into the stream of exhaust gas. The imperforate side wall 32 of the shield will preclude any direct bombardment of the cell with particulate matter in the exhaust stream. The nose 24 of the cell is recessed from the open mouth 34 of the shield. Nevertheless, contrary to conventional wisdom, the sensitivity of the cell is not impaired in this arrangement, and the heating of the cell, which is a prerequisite to its proper operation, is accomplished no less quickly than with conventional configurations. The easy replaceability of the cell is also a feature of this invention. In conventional sensor units, the entire unit must be replaced, at a current cost of up to two hundred dollars. In the present invention, the cell alone, which currently costs less than twenty dollars, can be replaced.

Referring now to FIGS. 9 through 15 for another embodiment of sensing unit of this invention, reference numeral 101 indicates an oxygen sensor unit of this embodiment, made up of a cell 102, a shell or shield 103, a plug 104 made up of a body 105 and a closure cap 106, a ceramic sleeve 107, a clip-terminal 108, a debris shield 109, washers 111 and 113, and a lead or terminal wire 115.

Figures 9, 10:
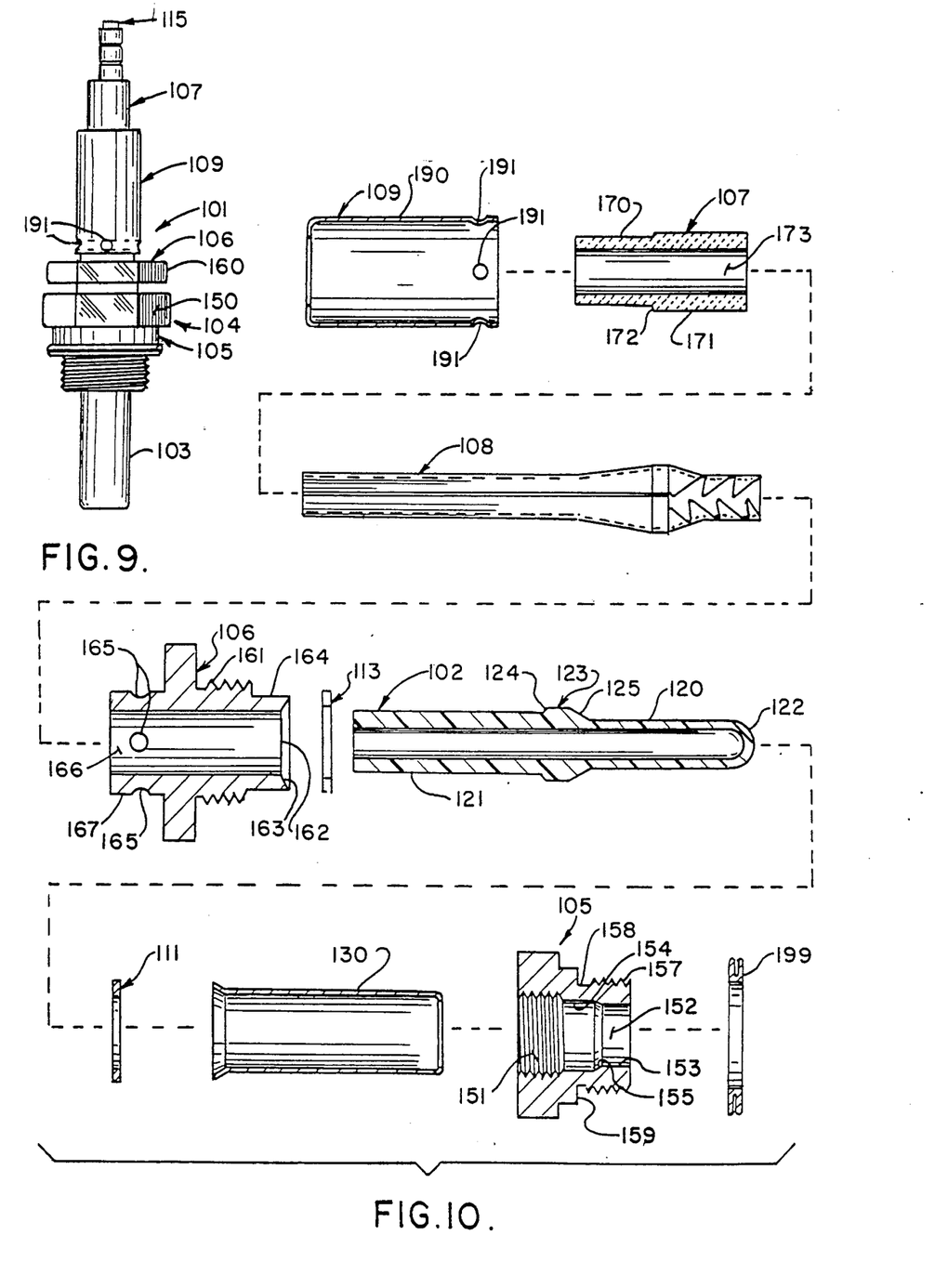
FIG. 9 is a view in side elevation of another embodiment of oxygen sensor of this invention.
FIG. 10 is an exploded sectional view of the device shown in FIG. 9.
Figure 11:
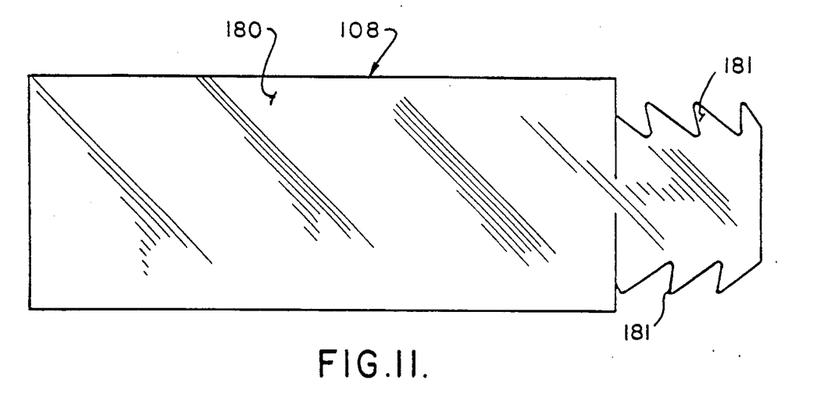
FIG. 11 is a top plan view of a terminal connector as it is stamped from a sheet.
Figure 15:
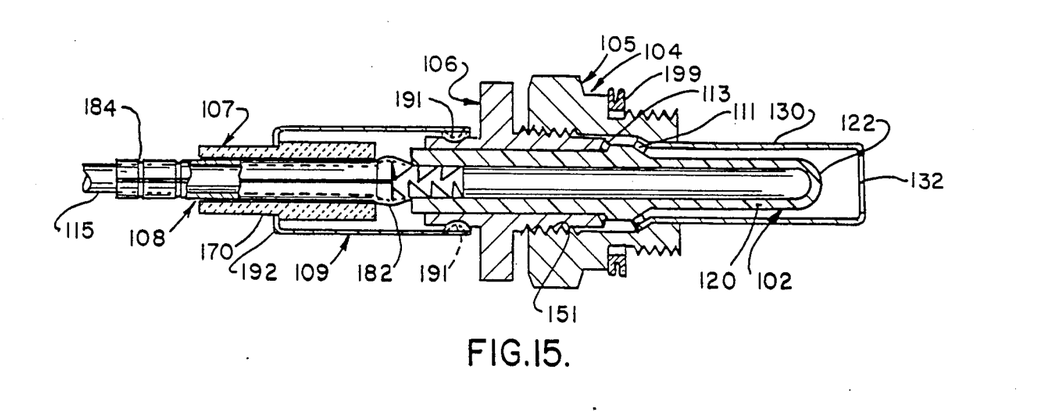
FIG. 15 is a longitudinal sectional view of an assembled oxygen sensor of the embodiment shown in FIGS. 9–14.

The cell 102, like the cell 2, is a hollow zirconia shape, but, unlike the cell 2, the cell 102 has a uniformly cylindrical inner section 120, a uniformly cylindrical outer section 121, which has a heavier wall than the inner section 120, a rounded closed inner end 122 and a shoulder 123, between the sections 120 and 121, the shoulder 123 having a chamfered outboard edge 124, and a chamfered inboard edge 125, providing seating surfaces for the washers 113 and 111, respectively. The cell 102 has a passage that is uniformly cylindrical from an open mouth to the closed end 122.

In respect of its having an inner and outer electrode, the cell is conventional.

The shell or shield 103 is a cylindrical tube of metal, as, for example, stainless steel, with an imperforate side wall 130 flared at its outer end form a lip 131. The shell has an open inner mouth 132.

The body 105 has hex flats to receive a wrench, an internally threaded section 151 concentric with a center passage 152, the diameter of an inner end 153 of which is necked down, relative to the diameter of an intermediate section 154, to define a shoulder 155. The body also has an externally threaded section 157 at its inner end, the threaded section 157 terminating at its outer end at a channel 158, one side of which is defined by a radial shoulder surface 159.

In this embodiment, the closure cap 106 has hex flats 160, intermediate the ends of the cap. On the inward side of the flats, external threads 161 terminate short of a cylindrical section 164, with a mouth 162, radially inwardly chamfered to form a seat area 163. On the outboard side of the flats, the cap has an outer cylindrical section 167 in which a plurality of dimples or detent seats 165 are formed. In this embodiment of cap, a central, uniformly cylindrical passage 166 extends all the way through the cap, to receive the outer section 121 of the cell, which extends through the cap and slightly beyond its outer end, as shown particularly in FIG. 15.

In this embodiment, the ceramic sleeve 107 has an outer neck section 170, a heavier-walled body section 171, a shoulder 72, between the sections 170 and 171, and a uniformly cylindrical central passage 173.

Figures 12, 13:
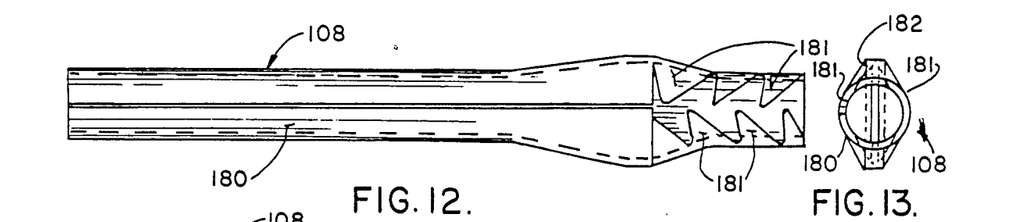
FIG. 12 is a top plan view of the connector of FIG. 11 in condition to be crimped to a terminal lead wire.
FIG. 13 is a view in end elevation, viewed from right to left of FIG. 12, of the terminal shown in FIG. 12.
Figure 14:
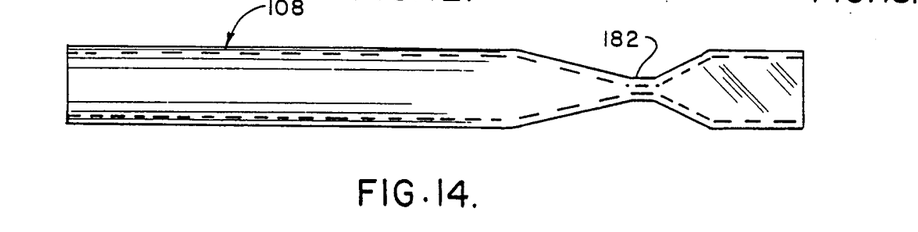
FIG. 14 is a top plan view of the terminal as oriented in FIG. 13.

The clip terminal 108 has a strap section 180 and serrated wings 181. After the terminal is rolled, as shown particularly in FIGS. 12, 13 and 14, an area contiguous and including a small part of the contact wing area, is flattened, as shown in FIGS. 12, 13 and 14, to increase the effective width of the clip-terminal in that area, both to serve as a stop, and as a means of obtaining good contact with the inner electrode surface of the cell in the assembled condition of the unit as shown in FIG. 15. The inner end of the wing section can also be spread prior to its insertion, if that is desired The terminal wire 115 is crimped into an outer, crimped area 184 of the strap portion 180.

The debris shield 109 has a cylindrical side wall 190, near the inner open mouth of which are ballnose detents 191 complementary to the dimples or detent receivers 165 in the closure cap 106. At its outer end, the debris shield has an inboardly turned ledge 192 proportioned to engage the shoulder 172 on the ceramic sleeve 107

A gasket 199 is mounted loosely in the channel 158 of the body 105, against the radial surface of the shoulder 159.

The assembly of this embodiment of sensor unit is believed to be self evident from FIGS. 10 and 15, particularly in view of the explanation of the assembly of the first embodiment. The chief difference from the first embodiment, as far as assembly is concerned, is that the washer 113 and closure cap 106 should be mounted on the outer section 121 of the cell 102 before the cap 106 is mounted in the body 105, and the ceramic sleeve 107 and the debris shield 109 should be mounted around the clip terminal 108 after the terminal wings are forced into the open end of the cell.

The debris shield 109 can simply be snapped into place, serving not only to protect the cell from contamination, but to help hold the ceramic sleeve, hence the clip terminal, against outward displacement. The debris shield can be removed by prying it off the cap. The disassembly of the sensor for the purpose of replacing the sensor cell will be evident from the description of the assembly.

Figure 16:
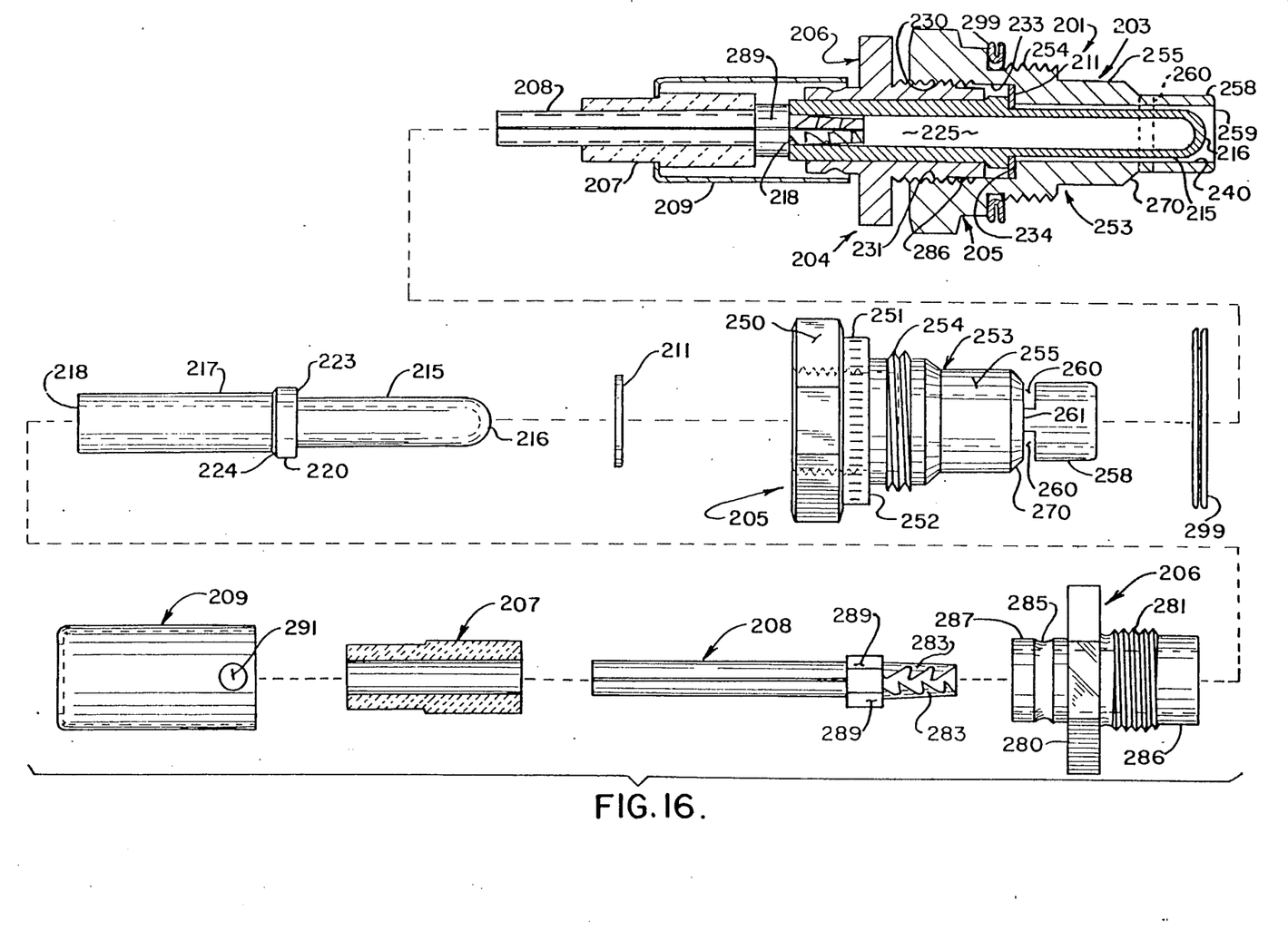
FIG. 16 is an exploded view, with the fully assembled sensor in section and the various components shown in side elevation, of yet another embodiment of sensor of this invention.

Referring now to FIG. 16 for yet another embodiment of sensing unit of this invention, reference numeral 201 indicates an oxygen sensor unit of this embodiment, made up of a cell 202, a shell or shield 203, a plug 204 made up of a lower body 205 and a closure or upper body 206, an insulator 207, a clip-terminal 208, a debris shield 209, a copper gasket 211, and a cell terminal 213.

The cell 202 has a uniformly cylindrical inner section 215 with a closed end 216 and a uniformly cylindrical outer section 217 of greater diameter than that of inner section 215, with an outer open end 218. A collar 220 projects radially from the outside surface of the cell between the inner and outer sections 215 and 217. The collar 220 has a radially flat annular surface 223 defining the outer edge of the inner section, and a chamfered outer surface 224 extending between the collar and the outer section 217. The cell 202 has a uniformly cylindrical bore 225 from its closed end 216 through its mouth 218.

The lower plug body 205 has a closure receiving section 230 with internal threads 231 and an intermediate, unthreaded section 233 ending at a radially inwardly extending annular flat surface defining a shoulder 234 marking the beginning of a heavywalled shield section 253. The heavy-walled shield section 253 includes an externally threaded section 254 and a heavy-walled heat sink section 255 of a diameter smaller than the threaded section 254, but larger than a nose section 258. A uniformly cylindrical passage 240 extends from an open end 259 of the nose section 258 to the shoulder 234, and is coaxial with the internally threaded closure receiving section 230 and intermediate section 233.

Where it meets the nose 258, the heavy-walled heat sink section 255 is chamfered to provide a slope 270. At the axially inner edge of the slope, radial slots 260 are cut chordally at the base of the nose in such a way as to leave a bridging neck 261, interrupting the continuity of the nose. It has been found that the slope 270 is important. An abrupt radially flat face does not produce the desirable results that a slope of 30 to 45 degrees produces Also, the ratio of the slot opening to the cell exhaust sensing area, the ratio of the end opening to the cell exhaust sensing area and the ratio of the total lower body openings to the cell exhaust sensing area are all important. In the illustrative embodiment described, the ratio of the end opening to the slot openings is about 3 to 1; the ratio of the cell exhaust sensing area to the area of the slot openings is about 6.5 to 1; the ratio of the cell exhaust sensing area to the end opening is about 2 to 1; and the ratio of the cell exhaust sensing area to the total area of the lower body openings is about 6 to 5. While these particular ratios are not critical, it will be observed that the end opening is approximately three times as large as the slot openings, and the exhaust sensing area of the cell is more than six times the area of the slot openings. The exhaust sensing area of the cell extends from its closed end 216 to the shoulder 223.

The closure or upper body 206 of this embodiment is similar to the closure 106 of the embodiment shown in FIGS. 9 and 10, with hex flats 280, external threads 281 and an outer cylindrical section 287. The closure 206 of this embodiment has a dimple-receiving channel 285. Inboard of the threaded section 281, the closure has a slightly tapered ring 286, the inboard edge of which engages the chamfered outer surface of the collar 220 when the device is assembled. The radially flat inner surface of the collar 220 engages the copper gasket 211, the other radial surface of which is seated against the shoulder 234 of the lower plug body. As in the case of the closure 106, the closure 206 has a central, uniformly cylindrical passage 288 through it, to accommodate the outer section 217 of the cell 202.

A plug gasket 299 is seated in a seat formed between the threaded section 254 and the shoulder 252, when the sensor is installed in an internally threaded boss of an exhaust manifold, for example.

The clip-terminal 208 of this embodiment has wire gripping wings 283 at its inner end. Spacer-locater wings 289 in this embodiment are closely adjacent the gripping wings 283, and serve the function of locating the gripping wings within the outer end of the cell and spacing the insulator 207 from the cell end, as shown clearly in the sectional view of the assembled sensor in FIG. 16.

The debris shield 209 has dimples 291 near its inner end, that snap into the channel 265, to cage the insulator 207 between the radially inturned rim of the shield 209 and the spacer-locater wings 289.

The embodiment shown in FIG. 16 and just described has certain special virtues The increased mass of the shield as an integral part of the lower plug body causes the sensor to stay near its critical functional temperatures for a longer period during extended idle and slow speed driving. After warm up, this construction enables the system closed loop control to function for extended periods under conditions of idle or slow speed driving. At the same time, the chordal slots, taken together with the sloped edge of the heavy section, enables the gases to circulate past the cell, enabling the cell to warm to operating temperature rapidly and producing sensor output voltages with minimal voltage fluctuations, eliminating wide variations in "instantaneous" fuel use and minimizing fluctuations away from stoichiometric air/fuel ratios.

The assembly and disassembly of the embodiment of sensor shown in FIG. 16 and described above, will be evident from the drawing and from the explanation of the assembly and disassembly of the other embodiments. As in the other two embodiments described, the lower plug body can be held by a wrench embracing the flats of the lower plug body against rotation with respect to the upper plug body or closure, while the upper plug body is backed out by means of another wrench embracing the flats on the upper plug body.

Numerous variations in the construction of the device of this invention, within the scope of the appended claims, will occur to those skilled in the art in the light of the foregoing disclosure. Merely by way of example, the cell in the second two embodiments can be tapered, as in the first embodiment, and the specific configuration of the various elements can be altered in other ways, as long as the cell shield has a side wall and the cell is recessed from the open mouth of the cell shield. Conventional stripes of conductor from the inner and outer electrode surfaces can be provided. Additional washers or gaskets can be employed, as, for example, around the neck 70 of the ceramic sleeve, to be compressed between the shoulder 72 of the sleeve and shoulder 64 in the cap, and other provisions made to anchor the lead wire 15 against accidental dislodgment or loosening from the cell. These are merely illustrative.

Having thus described the invention, what is claimed and desired to be secured by Letters Patent is:

1. An oxygen sensing unit including a plug having an externally threaded closure cap and an internally threaded body, an oxygen sensing hollow cell with a closed outer end, and a protective shield, said cell being removably and replaceably mounted in said plug with parts thereof compressed mediately or immediately between said cap and said body, said protective shield being integral with a portion of said plug, said shield having a heavy-walled section and a nose section of lesser outside diameter than said heavy-walled section, chordal slots in said nose section contiguous said heavy-walled section communicating with a passage in which said cell is mounted, an axially outboard wall defining the outboard edge of said slots having, radially outboard of the said slots, a sloped surface making an acute angle with the axis of said passage.

2. In an oxygen sensing unit having an oxygen sensing cell, a protective shield around at least a portion of said cell, and a plug having a body, the improvement comprising means for selectively removably mounting said cell and shield in said body to project therefrom into a stream of gas, said mounting means including a closure cap selectively mountable and demountable on said body for holding said cell and shield in said body, and a debris shield selectively demountably mounted on said closure cap.

3. The oxygen sensing unit of claim 2 including an electrically insulative sleeve caged by said debris shield.

4. The oxygen sensing unit of claim 2, wherein said insulating sleeve is a ceramic sleeve mounted in said closure cap, said unit including a terminal lead wire and an elongated terminal lead wire clip-terminal, said clip-terminal being mounted in electrical contact with an interior surface of said cell at one end, and in electrical contact with said terminal lead wire at its other end, extending through said ceramic sleeve and debris shield and projecting outwardly therefrom.

5. The oxygen sensing unit of claim 4 wherein said clip-terminal is tubular through a portion of its length and has a flattened portion positioned between said cell and said sleeve contiguous the outer end of said cell and the inner end of said sleeve, said flattened portion being of a greater width than the inside diameter of the cell and the sleeve and serving as a positioning means for said sleeve and said clip terminal with respect to said cell.

6. An oxygen sensing unit including a plug having an externally threaded closure cap or upper plug body and an internally threaded lower plug body, an oxygen sensing hollow cell with a closed outer end, and a protective shield, said cell being removably and replaceably mounted in said plug with parts thereof compressed mediately or immediately between said cap and said body, said protective shield being integral with said lower plug body, said shield having a heavy-walled section and a nose section, chordal slots in said nose section contiguous said heavy-walled section communicating with a passage in which said cell is mounted, an axially outboard wall defining the outboard edge of said slots having, radially outboard of the said slots, a sloped surface making an acute angle with the axis of said passage.

7. In an oxygen sensing unit having an oxygen sensing hollow cell with a closed outer end, and a protective, elongated cylindrical shield with a passage extending axially through it to receive said cell, the improvement comprising said shield having a heavy-walled part and a nose of lesser outside diameter than the heavy-walled part, integral with said heavy-walled part, said shield having an open outer end, said cell terminating short of the open outer end of said shield, said shield having chordally extending slots, communicating with said passage, across the nose contiguous the said heavy-walled part, said heavy-walled part having a chamfered edge ending immediately contiguous the said slots to define a slope making an inwardly convergent acute angle with the axis of said shield.

8. The improvement of claim 7 wherein the ratio of the oxygen sensing area of the cell to the area of the open outer end is on the order of two to one, and the ratio of the oxygen sensing area of said cell to the area of said chordal slots in communication with said passage is on the order of at least six to one.

9. In an oxygen sensing unit including a plug having a closure cap and a body adapted to be mounted to extend into a steam of exhaust gas, an oxygen sensing hollow cell with a closed outer end, and a protective shield, said cell being removably and replaceably mounted in said plug and extending into an axially extending passage in said body, the improvement comprising said protective shield being integral with said body, said shield having a heavy-walled section and a nose section, at least one opening in said nose section contiguous said heavy-walled section communicating with said passage in which said cell is mounted, said heavy-walled section having, contiguous said opening, radially outboard of said opening, a sloped surface making an acute angle with the axis of said passage convergently toward said opening.

10. In an oxygen sensing unit including a plug having a closure cap and a body adapted to be mounted to extend into a stream of exhaust gas, an oxygen sensing hollow cell with an open inner end and a closed outer end, and a protective shield, said cell being removably and replaceably mounted in said plug with parts thereof compressed mediately or immediately between said cap and said body, said cell having an inner surface and an outer surface, the improvement comprising a terminal lead wire and an elongated terminal lead wire clip-terminal, said clip-terminal having serrated wings mounted in mechanical and electrical contact with said inner surface at one end of said clip terminal, wire gripping means crimped to a bare section of said terminal lead wire, and means integral with said clip terminal, extending radially outwardly with respect to said wings, abutting said inner end of said cell and limiting the distance the said wings extend into said cell.

11. In an oxygen sensing unit including a plug having a closure cap and an externally threaded body, and a hollow elongated oxygen sensing cell with a closed outer end, the improvement comprising said plug body being of one-piece construction, having an axially extending passage within which said cell is mounted, a heavy-walled section contiguous said threaded section and a nose section of an outside diameter less than the outside diameter of said heavy-walled section projecting from said heavy-walled section in a direction toward said closed end of said cell, said heavy-walled section having a surface sloped convergently toward said closed end to meet said nose section and at least one aperture communicating with said passage through a wall of said nose section contiguous the juncture of said sloped surface and said nose section.

* * * * *